United States Patent [19]

Ayer

[11] Patent Number: 4,627,971
[45] Date of Patent: Dec. 9, 1986

[54] OSMOTIC DEVICE WITH SELF-SEALING PASSAGEWAY

[75] Inventor: Atul D. Ayer, Mt. View, Calif.
[73] Assignee: ALZA Corporation, Palo Alto, Calif.
[21] Appl. No.: 725,832
[22] Filed: Apr. 22, 1985
[51] Int. Cl.[4] .................. A61K 9/26; A61K 9/24; A61J 3/00
[52] U.S. Cl. .............................. 424/15; 424/22
[58] Field of Search ................................ 424/22, 15

[56] References Cited

U.S. PATENT DOCUMENTS

| | | | |
|---|---|---|---|
| 3,402,240 | 9/1968 | Cain et al. | 424/22 |
| 3,916,899 | 11/1975 | Theeuwes et al. | 424/15 |
| 4,088,864 | 5/1978 | Theeuwes et al. | 424/15 |
| 4,210,139 | 7/1980 | Higuchi | 424/19 |
| 4,265,874 | 5/1981 | Bonsen et al. | 424/15 |
| 4,327,725 | 5/1982 | Cortese et al. | 424/19 |
| 4,434,153 | 2/1984 | Urquhart et al. | 424/22 |
| 4,449,983 | 5/1984 | Cortese et al. | 424/25 |

*Primary Examiner*—Ronald W. Griffin
*Attorney, Agent, or Firm*—Paul L. Sabatine; Edward L. Mandell; Steven F. Stone

[57] ABSTRACT

An osmotic dispensing device is disclosed for delivering a medicine to a biological environment of use. The device comprises a semipermeable wall surrounding a compartment comprising a first layer comprising a beneficial agent formulation and a first passageway in the wall for delivering the beneficial agent formulation from the device, and a second layer of a composition comprising a hydrogel and a means for closing a second passageway formed during the manufacture of the device.

2 Claims, 9 Drawing Figures

OSMOTIC DEVICE WITH SELF-SEALING PASSAGEWAY

FIELD OF THE INVENTION

The present invention pertains to both a novel and useful osmotic device for dispensing a beneficial agent formulation. More particularly the invention concerns an osmotic device comprising a compartment containing (1) a beneficial agent formulation, and (2) an expandable hydrogel for delivering the beneficial agent from the compartment containing means for closing a passageway formed during the manufacture of the osmotic device. The invention concerns also a process for manufacturing an osmotic device.

BACKGROUND OF THE INVENTION

Osmotic devices for delivering a beneficial agent formulation, including a medicine, to an enivornment of use are known to the prior art in U.S. Pat. No. 3,845,770 issued to Theeuwes and Higuchi, and in U.S. Pat. No. 3,916,899 issued to the same patentees. The osmotic devices disclosed in these patents comprise a semipermeable wall that surrounds a compartment containing a beneficial agent formulation including a medicinal formulation. The semipermeable wall is permeable to the passage of an external fluid present in the environment of use and it is substantially impermeable to the passge of a beneficial agent formulation. An osmotic passageway is provided through the wall for delivering the beneficial agent formulation from the osmotic device. These prior art devices release the beneficial agent formulation by imbibing fluid through the semipermeable wall into the compartment to form in the compartment an aqueous solution containing the beneficial agent formulation that is delivered through the passageway from the osmotic device. The external fluid is imbibed through the semipermeable wall into the compartment in a tendency towards osmotic equilibrium at a rate determined by the permeability of the semipermeable wall and the osmotic pressure gradient across the wall. These devices are extraordinarily effective for delivering a beneficial agent formulation that is soluble in the fluid and exhibits an osmotic pressure gradient across the semipermeable wall against the external fluid. These osmotic devices are extraordinarily effective also for delivering a beneficial agent formulation that has limited solubility in the external fluid and is admixed with an osmotically effective osmagent that is soluble in the fluid and exhibits an osmotic pressure gradient across the semipermeable wall against the fluid. The beneficial agent formulation is incorporated into these osmotic devices during their manufacture, prior to forming the semipermeable wall around the compartment. These prior art osmotic devices operate successfully for delivering a beneficial agent formulation including a beneficial medicinal formulation to an environment of use.

A pioneering advancement in osmotic delivery devices was presented to the dispensing art by Cortese and Theeuwes in U.S. Pat. No. 4,327,725. In this patent, the delivery kinetics of the osmotic device are enhanced for delivering beneficial agents with degrees of solubility in aqueous films that are difficult to deliver, such as very soluble or insoluble in the fluid. For these beneficial agents, the delivery kinetics are enhanced by placing in the compartment an expandable driving member that urges the agent formulation through a passageway from the device. The expandable driving member is formed of a water-expandable hydrogel that absorbs fluid imbibed into the compartment and expands from a rested to an expanded state. The hydrogel is in contact with the agent formulation with the hydrogel positioned distant from the passageway. As the hydrogel absorbs fluid it increases in volume causing it to exert force against the agent formulation, thereby urging the agent formulation through the passageway over time.

The osmotic passageway, in the osmotic device described immediately above, is laser drilled through the semipermeable wall to connect a beneficial agent dye-free formulation with the exterior of the osmotic device. The osmotic passageway is laser drilled in this predetermined location by orienting the osmotic device such that the laser drills a passageway only at this loci. This orientation is made possible by adding a dye to the expandable hydrogel and then scanning the exterior of the osmotic device for a difference in shade between the beneficial agent dye-free formulation and the expandable dye-containing hydrogel. The presence of the dye imparts a shade to the expandable hydrogel exhibited as a comparative darkness as seen through the translucent semipermeable wall.

The above described prior art procedure is remarkably successful for laser drilling the osmotically calibrated passageway, even though it requires the use of a comparative light-producing agent, visual observation, or optical scanning for positioning the osmotic device. It will be appreciated, by those versed in the dispensing art, that if an osmotic device is provided that does not require the orientation, or the agent, or the scanning techniques of the prior art, such an osmotic device would represent an inventive contribution and an unobvious and a practical advancement in the dispensing art.

OBJECTS OF THE INVENTION

It is, accordingly, an immediate object of this invention to provide both a novel and useful osmotic device that fulfills the needs of the dispensing art and is easier to manufacture, thereby avoiding the requirements of the prior art.

Another object of the invention is to provide an osmotic device that can be made free of the orientation procedure of the prior art.

Another object of the invention is to provide an osmotic device comprising an osmotic passageway and a self-sealed passageway.

Another object of the invention is to provide an osmotic device comprising a compartment containing means for closing a passageway formed during the manufacture of the osmotic device.

Another object of the invention is to provide an osmotic device having a compartment comprising a beneficial agent formulation, and an expandable driving member formed of a layer of a hydrogel having means for sealing a passageway blended therein.

Another object of the invention is to provide an osmotic device having a compartment housing a beneficial agent formulation that can be from insoluble to very soluble in an aqueous fluid, and in expandable driving member comprising a hydrogel and means for sealing a passageway in the wall of the osmotic device, and which hydrogel can generate a force that acts to diminish the volume occupied by the beneficial agent formulation, thereby substantially maintaining the beneficial agent formulation in a saturated state during its release from the osmotic device.

Another object of the invention is to provide an osmotic device comprising a semipermeable wall surrounding a compartment containing a layer of a beneficial agent formulation and a layer of an expandable driving member consisting essentially of a hydrogel and means responsive to thermo energy for forming a film and for sealing a passageway.

Another object of the invention is to provide an osmotic device comprising a semipermeable wall surrounding a compartment comprising a layer of a beneficial agent formulation and a layer formed of a hydrogel and means for forming a film and for closing a passageway, and which osmotic device comprises an opened passageway in the wall communicating with the layer of agent and a closed passageway in the wall communicating with the layer of hydrogel.

Another object of the invention is to provide an osmotic therapeutic device that can administer a complete pharmaceutical regimen comprising soluble to very soluble medicinal agents or poorly soluble medicinal agents at a controlled and continuous rate to a warm-blooded animal, for a particular time period, the use of which requires intervention only for initiation and possible termination of the regimen.

Another object of the invention is to provide a process for manufacturing an osmotic device comprising an opened passageway and a closed passageway.

BRIEF DESCRIPTION OF THE DRAWINGS

In the drawings, which are not drawn to scale, but are set forth to illustrate various embodiments of the invention, the drawing figures are as follows.

In the drawing figures and in the specification like parts in related figures are identified by like numbers. The terms appearing earlier in the specification and in the description of the drawing figures, as well as embodiments thereof, are further detailed elsewhere in the disclosure.

DETAILED DESCRIPTION OF THE DRAWINGS

Figure 1:
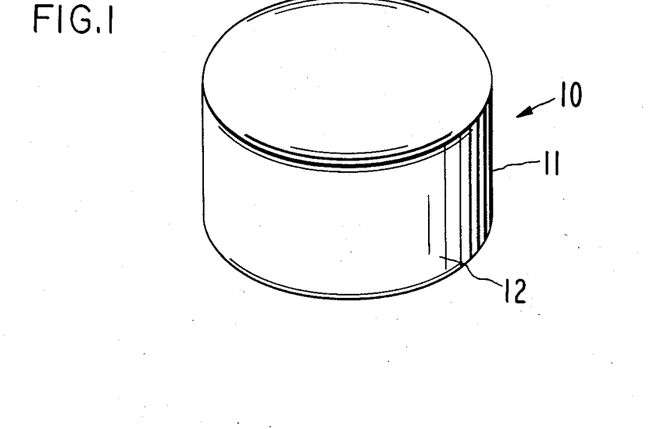
FIG. 1, is a view of an osmotic dispensing device designed and adapted for administering orally a beneficial agent formulation to the gastrointestinal tract.
Figure 2:
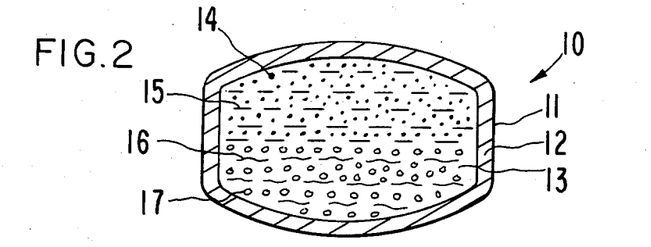
FIG. 2 is an opened view of the osmotic dispensing device of FIG. 1, with FIG. 2 illustrating the internal and the external structure of the osmotic dispensing device.
Figure 3:
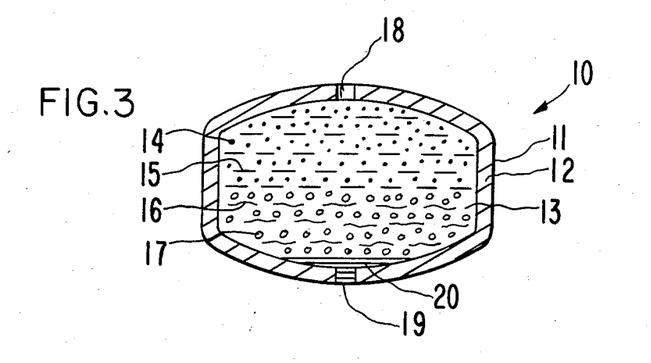
FIG. 3 is an opened view of the osmotic dispensing device of FIGS. 1 and 2, with FIG. 3 depicting an opened osmotic passageway and a closed osmotic passageway in the wall of the osmotic device.

Turning now to the drawing figures in detail, which are examples of various osmotic delivery devices provided by the invention, and which examples are not to be construed as limiting, one example of an osmotic device is seen in FIGS. 1 through 3 considered together. In FIG. 1, an osmotic device 10 is seen comprising a body member 11 having a wall 12 that surrounds an internal compartment not seen in FIG. 1.

In FIG. 2, osmotic dispensing device 10 is seen in opened section. In FIG. 2, osmotic device 10 comprises body 11, wall 12 and internal compartment 13. Wall 12 is formed of a polymeric composition that is substantially permeable to the passage of an external fluid present in the environment of use, and it is substantially impermeable to the passage of a beneficial agent formulation, osmagent and osmopolymer. The semipermeable polymer forming wall 12 is non-toxic and it maintains its physical and chemical integrity during the dispensing life of osmotic device 10.

Internal compartment 13 of osmotic device 10 comprises a layer of a beneficial agent formulation 14 including a beneficial medicinal formulation identified by dots 14. The beneficial agent formulation 14 can be from insoluble to very soluble in an aqueous fluid, indicated by dashes 15, that is imbibed into internal compartment 13. Compartment 13 in another embodiment can contain a layer of beneficial agent 14 that has limited solubility in fluid 15 and exhibits an osmotic pressure gradient across wall 12 against an external fluid. When beneficial agent formulation 14 has limited solubility it can be mixed with an osmagent or with an osmopolymer that is soluble in the external fluid and exhibits an osmotic pressure gradient across wall 12 against the exterior fluid present in the environment of use.

Compartment 13 further houses a layer of an expandable driving composition comprising a hydrogel 16 identified by wavy lines, and a means for sealing a passageway formed during the manufacture of osmotic device 10 and identified by circles 17. Hydrogen 16 is a hydrophilic water insoluble polymer, optionally lightly cross-linked. Hydrogel 16 possesses osmotic properties such as the ability to imbibe an external fluid and exhibit an osmotic pressure gradient across semipermeable wall 12 against the external fluid. Hydrogel 16 absorbs fluid imbibed into compartment 13 and swells or expands to some equilibrium state. At equilibrium the osmotic pressure of hydrogel 16 approximately equals the swelling pressure of the hydrogel, and the osmotic pressure of the hydrogel 16 network is the driving force of expanding member 16. Hydrogel 16 is in immediate contact with beneficial agent 14 and at their interface it applies direct force against beneficial agent formulation 14. This force urges the agent formulation to be delivered from osmotic device 10 during operation of osmotic device 10.

Means 17, as seen in circles in FIG. 2, is present for sealing or closing a passageway formed during manufacture of osmotic device 10. Means 17 is formed of a material that exhibits the ability to flow and form a film, or close a passageway under the influence of laser energy. That is, during the manufacture of osmotic device 10, as seen in FIG. 3, a first and opened passageway 18 is laser drilled through semipermeable wall 12 connecting the exterior of device 10 with compartment 13 for delivering beneficial agent 14 to the environment of use. Also, during the manufacture of osmotic device 10, a second passageway 19 is laser drilled through semipermeable wall 12. Passageway 19 is drilled on the opposite surface of osmotic device 10 distant from passageway 18. Passageway 19 is drilled by turning over osmotic device 10. In an optional manufacturing embodiment, passageway 19 is drilled followed by drilling passageway 18, or passageways 18 and 19 can be drilled at one time by holding the device in one position. Laser machines with photo detecting means for orienting a device and then laser drilling a passageway are known to the prior art in U.S. Pat. No. 4,063,064 and in U.S. Pat. No. 4,088,864. During the manufacture of passageway 19, means 17 self-seals passageway 19. Means 17 is formed of a material that exhibits the ability to flow and form a film or close a passageway under the influence of laser energy. Means 17, under the influence of thermo-laser energy, about 500° C. to 700° C., melts, becomes soft and forms a film 20. Film 20 is a self-sealing means for closing over or for plugging passageway 19, thereby producing a closed passageway. Osmotic device 10, as manufactured herein, osmotically and hydrodynamically delivers beneficial agent formulation 14 through passageway 18 to an environment of use, including a biologic environment of use.

FIGS. 1 through 3 depict one presently preferred embodiment of osmotic device 10. In this embodiment device 10 is made for oral use, that is, for releasing a locally acting medicine, or a systemically active medicine in the gastrointestinal tract. The oral system can have various shapes and sizes. In one design, device 10 can be curved, eliptical, such as round, with a diameter of $\frac{1}{8}$ inch to 9/16 inch, or it can be shaped like a capsule having a range of sizes from triple zero to zero, and from 1 to 8.

While FIGS. 1 through 3 illustrate one dispensing device that can be made according to the invention, it is to be understood device 10 can take a wide variety of shapes, sizes and forms for delivering a beneficial agent including a medicine to the environment of use. For example, the osmotic devices include buccal, implant, artificial gland, cervical, intrauterine, nose, veterinary, and the like osmotic devices. In these forms device 10 can be adapted for administering a beneficial medicine to numerous animals, warm-blooded mammals, humans, avians and reptiles. The device also can be sized, shaped structured and adapted for delivering an active agent in streams, aquariums, fields, factories, reservoirs, laboratory facilities, hot houses, transportation means, naval means, military means, hospitals, veterinary clinics, nursing homes, farms, zoos, sickrooms, chemical reactions and other environment of use.

DETAILED DESCRIPTION OF THE INVENTION

In accordance with the practice of the invention, it now has been found that osmotic delivery device 10 can be manufactured with a wall 12 formed of a material that does not adversely affect beneficial agent 14, which includes drug, and it does not adversely affect an osmagent, a hydrogel, an animal, or a host. Wall 12 is formed of polymeric composition permeable to the passage of an external aqueous-type fluid such as water and biological fluids, while remaining essentially impermeable to the passage of beneficial agent 14 which includes drug, osmagent, and the like. The selectively semipermeable materials forming wall 12 are insoluble in fluids, and they are non-erodible, hence they maintain their physical and chemical integrity during the operation of the osmotic device in the environment of use.

Typical materials for forming wall 12 include semipermeable polymers known to the art as osmosis and reverse osmosis membranes. These include cellulose ester, cellulose ether, cellulose ester-ether, cellulose acylate, cellulose diacylate, cellulose triacylate, cellulose acetate, cellulose diacetate, cellulose triacetate, agar acetate, amylose triacetate, beta glucan acetate, cellulose acetaldehyde dimethyl acetate, cellulose acetate ethyl carbamate, cellulose acetate methyl carbamate, cellulose acetate succinate, cellulose acetate dimethylaminoacetate, cellulose acetate ethyl carbamate, cellulose acetate chloroacetate, cellulose dipalmate, cellulose dioctanoate, cellulose dicaprylate, cellulose dipentanlate, cellulose acetate valerate, cellulose acetate succinate, cellulose propionate succinate, cellulose acetate p-toluene sulfonate, cellulose acetate butyrate, cross-linked selectively semipermeable polymers formed by the coprecipitation of a polyanion and a polycation as disclosed in U.S. Pat. Nos. 3,173,876; 3,276,586; 3,541,005; 3,541,006, and 3,546,142; semipermable polymers as disclosed by Leob and Sourirajan in U.S. Pat. No. 3,133,132; lightly cross-linked semipermeable polystyrene derivative, cross-linked semipermeable poly(sodium styrene sulfonate), semipermeable poly(vinylbenzyltrimethylammonium chloride), cellulose acetate having a degree of substitution up to 1 and an acetyl content up to 21%, cellulose diacetate having a degree of substitution of 1 to 2 and an acetyl content of 21% to 35%, cellulose triacetate having a degree of substitution of 2 to 3 and an acetyl content of 35% to 44.8%, as disclosed in U.S. Pat. No. 4,160,020. Generally, semipermeable materials useful for forming wall 12 will have a fluid permeability of $10^{-5}$ to $10^{-1}$ (cc/mil/cm$^2$ hr/atm) expressed per atmosphere of hydrostatic or osmotic pressure difference across semipermeable wall 12 can be used for the intended purpose.

The expression beneficial agent formulation and beneficial medicine formulation as used herein denotes a beneficial drug neat, and a composition comprising a beneficial drug and an osmagent. In the sepecification and the accompanying claims, the term medicine includes drug, and the term drug includes any physiologically or pharmacologically active substance that produces a local or systemic effect in animals, including warm-blooded mammals, human and primates, fishes, reptiles, farm, sport and zoo animals. The term 'physiologically' as used herein denotes the administration of a drug to produce normal levels and functions. The term 'pharmacologically' denotes variations in response to amount of drug administered to the host. *Stedman's Medical Dictionary*, 1966, published by Williams and Wilkins, Baltimore, MD. The active drug that can be delivered includes inorganic and organic drugs without limitations, those drugs that act on the central nervous system, depressants, hypnotics, sedatives, psychic energizers, tranquilizers, anticonvulsants, muscle relaxants, anti-parkinson agents, analgesics, anti-inflammatory, local anesthetics, muscle contractants, anti-microbials, anti-malarials, hormonal agents, contraceptives, sympathomimetics, diuretics, anti-parasitics, neo-plastics, hypoglycemics, opthalmics, electrolytes, diagnostic agents and cardiovascular drugs. The amount of beneficial agent formulation 14 housed in compartment 13 generally is from about 10 nanograms to 350 milligrams, or more.

Exemplary drugs that can be carried on the core member and delivered by the osmotic device of this invention include prochlorperazine edisylate, prochlorperazine maleate, prazosin hydrochloride, clonidine hydrochloride, hydralazine hydrochloride, dextromethorpan hydrobromine, dextroamphetamine phosphate, diethylpropionm hydrochloride, isoxsuprine hydrochloride, ambenonium chloride, phenoxybenzamine hydrochloride, phentolamine hydrochloride, guanethidine sulfate, clidinium bromide, blycopyrrolate, homatropine methylbromide, hyoscyamine hydrobromide, mepenzolate bromide, methscopolamine bromide, balofen, and the like. These drugs and their daily dose are known to the art in *Pharmaceutical Sciences*, by Remington, 16th Ed., 1980, published by Mack Publishing Company, Easton, PA.

The medicine can be in various forms, such as uncharged molecules, molecular complexes, pharmacologically acceptable salts such as hydrochlorides, hydrobromides, sulfate, laurylate, palmitate, phosphate, nitrite, borate, acetate, maleate, tartrate, oleate and salicylate. For acid medicine, salts of metals, amines or organic cations, for example, quaternary ammonium can be used. Derivatives of medicine such as ester, ethers and amides can be used. Also, a medicine that is water insoluble can be used in a form that is a water soluble derivative thereof to serve as a solute and, on its release from the devices, it is converted by enzymes, hydrolyzed by body pH or other metabolic process to the original biologically active form.

The osmagent present in osmotic device 10, when used according to the mode of the invention, are osmotically effective compounds soluble in fluid that enter the device and exhibit an osmotic pressure gradient across the semipermeable wall against the exterior fluid. Osmotically effective osmagents useful for the present purpose include magnesium sulfate, magnesium chloride, sodium chloride, lethium chloride, potassium sulfate, sodiumcarbonate, sodium sulfite, lithium sulfate, potassium chloride, sodium sulfate, d-mannitol, urea insitol, raffinose, glycose, mixtures thereof, and the like. The osmagent is usually present in an excess amount, and it can be in any physical forms, such as particle, powder, granule and the like. The osmotic pressure in atmospheres, atm, of the osmagents suitable for the invention will be greater than zero atm, generally from zero atm up to 500 atm, or higher. The osmotically effective compounds are known to the art in U.S. Pat. Nos. 4,177,256 and 4,449,983.

The hydrogel suitable for the purpose of this invention are the expandable, driving swellable hydrophilic polymers, known to the dispensing art as osmopolymers. The swellable hydrophilic polymers are noncrosslinked and in a presently preferred embodiment they are lightly cross-linked, such cross-links being formed by covalent or ionic bond, which interact with water and aqueous biological fluids and swell or expand to some equilibrium state. The hydrogels exhibit the ability to swell in water and retain a significant fraction of water within its structure, and when cross-linked they will not dissolve in the water. The hydrogels can be of plant and animal origin, hydrogels prepared by modifying naturally occurring structures, and synthetic polymer hydrogels. The polymers swell or expand to a very high degree, usually exhibiting a 2 to 50 fold volume increase. Hydrophilic polymeric materials for the purpose include poly(hydroxyalkyl methacrylate), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methyl cellulose cross-linked with dialdehyde, a mixture of cross-linked agar and carobxymethyl cellulose, a water insoluble, water-swellable copolymer produced by forming a dispersion of finely divided copolymer of maleic anhydride with styrene, ethylene, propylene, butylene, or isobutylene cross-linked with from 0.001 to about 0.5 moles of a polyunsaturated cross-linked agent per mole of maleic anhydride in the copolymer, water-swellable polymers of N-vinyl lactams, cross-linked polyethylene oxides, and the like.

Other hydrogels include hydrogels exhibiting a cross-linking of 0.05 to 60%, hydrophilic hydrogels known as Carbopol® acidic carboxy polymer, Cyanamer® polyacrylamides, cross-linked, water-swellable indenemaleic anhydride polymers, Good-rite® polyacrylic acid, polyethyleneoxide, starch graft copolymers, Aqua-Keeps® acrylate polymer, diester cross-linked polyglucan, and the like. The hydrogels are known to the prior art in U.S. Pat. No. 3,865,108 issued to Hartop; in U.S. Pat. No. 4,022,173 issued to Manning; in U.S. Pat. No. 4,207,893 issued to Michaels, and in *Handbook of Common Polymers* by Scott and Roff, published by the Chemical Rubber Company, Cleveland, OH.

The expression "means for forming a film or for self-sealing a passageway" as used for denoting means 16 generically denotes any film-forming material or passageway closing material that is a solid at room temperature of 65° F. to 75° F. (18° C. to 24° C.) and readily melts, or flows under the influence of applied laser energy and then solidifies on cooling to room temperature. Means 16 for the purpose of this invention embraces waxes. The term "wax" generically denotes an ester of a high molecular weight fatty acid with a high molecular weight alcohol. The waxes acceptable for the present purpose exhibit a melting point or a solidification point of about 30° C. to 110° C., and they are selected from the group consisting of mineral, vegetable, plant, animal and synthetic waxes. Representative waxes include a member selected from the group consisting essentially of paraffin wax, such as hard paraffin wax and soft paraffin wax; montan; Hoechst; ozokerite; carnauba; palm; myricyl cerotale; beeswax including yellow and white bee wax; spermaceti, ceresine; Fischer-Tropsch; gama; Japan; myrtle; ouricury; esparto; flax; sugarcane; wool; acrowax; castor; opal, and the like. Waxes are known to the prior art in Hackh's *Chemical Dictionary*, 4th Ed., published in 1969 by McGraw-Hill Co., New York; and in *Handbook of Chemistry*, Lange, 12th Ed., Tables 709, 1979, published by McGraw-Hill Co., San Francisco. Means 16 also includes polymers having melting points below 200° C., usually in the range of 50° C. to 200° C. Representative polymers include a member selected from the group consisting of poly(ethylene) exhibiting a melting point, MP, of 137° C.; poly(acrylic acid, allyl ester) MP of 90° C.; poly(1,4-B-D-glucose, tricaprylate), MP of 116° C.; 1,4-poly(1,3-butadiene, 1-methoxy), MP of 118° C.; 1,4-poly(1,3-butadiene, 2-methyl-acetoxy), MP of 135° C.; poly(lactic acid), MP of 122° C.; poly(acrylic acid, sec-butyl ester), MP 130° C.; poly(acrylic acid, isopropyl ester), MP of 162° C.; poly(methylvinyl ether), MP of 144° C.; poly(tetramethylene isophthalate), MP of 152° C.; 1,2-poly(1,3-butadiene, 4,4-dimethyl), MP of 167° C.; poly(vinylmethyl ketone), MP of 170° C.; poly(3-hydroxy butyric acid), MP of 176° C.; poly(methacrylic acid, methyl ester), MP of 160° C.; poly(3-aminopropionic acid, 2,2-dimethyl-1), MP of 189° C.; and the like. Polymers acceptable for the present purpose include olefin and vinyl polymers within the designated temperatures; condensation polymers; and the like. The polymers are known to the prior art in *Polymer Handbook*, by Brandrup and Immergut, 1975, published by Wiley-Interscience, New York; and in *Handbook of of Common Polymers*, by Scott and Roff, 1976, published by CRC Press, Cleveland, OH.

The imbibition pressure of an osmopolymer as used for selecting an osmopolymer can be made by following the procedure. A ½ inch round disc, fitted with a ½ inch diameter stainless steel plug, is charged with a known quantity of polymer with the plugs extending out either end. The plugs and the die were placed in a Carver press with plates between 200° F. and 300° F. A pressure of 10,000 to 15,000 psi was applied to the plugs.

After 10 to 20 minutes of heat and pressure the electrical heating to the plates was turned off, and tap water circulated through the plates. The resulting ½ inch discs were placed in an air suspension coater charged with 1.8 kg saccharide cores and coated with cellulose acetate having an acetyl content of 39.8% dissolved in 94:6 wt/wt, $CH_2CL_2/CH_3OH$, to yield a 3% wt/wt solution. The coated systems were dried overnight at 45° C. The coated discs were immersed in water at 37° C., and periodically removed for gravimetric determination of water imbibed. The initial imbibition pressure was calculated by using the water transmission constant for the cellulose acetate, after normalizing imbibition values for membrane surface area and thickness. The polymer used in this determination was the sodium derivative of Carbopol-934 ® polymer, prepared according to the procedure of *B. F. Goodrich Service Bulletin GC-36* "Carbopol ® Water-Soluble Resins", p 5, published by B. F. Goodrich, Akron, OH.

The cumulative weight gain values, y as a function of time, t, for the water soluble polymer disc coated with the cellulose acetate were used to determine the equation of the line $y = c + bt + at^2$ passing through those points by a least square fitting technique.

The weight gain for the NaCarbopol-934 ® is given by equation as follows: Weight gain equals $0.359 + 0.655t - 0.00106t^2$ wherein t is elapsed time in minutes. The rate of water flux at any time will be equal to the slope of the line that is given by the following equation:

$$dy/dt = d(0.359 + 0.665t - 0.00106t^2)/dt$$

$$dy/dt = 0.0665 - 0.002t$$

To determine the initial rate of water flux the derivative is evaluated at $t = 0$, and $dy/dt = 0.665$ µl/min., which is equal to the coefficient b. Then, normalizing the imbibition rate of time, membrane surface area and thickness, the membrane permeability constant to water, $K\pi$, may be determined according to the following equation:

$$K\pi = 0.665 \,\mu l/\min \times (60 \min/hr) \times (1 \, ml/1000 \,\mu l)(0.008 \, cm/2.86 \, cm^2)$$

with $K\pi = 1.13 \times 10^{-4}$ cm²/hr. The $\pi$ value for NaCl was determined with a Hewlett-Packard vapor pressure osmometer to be 345 atm±10% and, the K value for cellulose acetate used in this experiment calculated from NaCl imbibition values to be $2.1 \times 10^{-7}$ cm²/hr.atm.

Substituting into the calculated K expression $(2.1 \times 10^{-7} /cm^2/hr.atm)$ $(\pi) = 1.13 \times 10^{-4}$ cm²/hr. $\pi = 600$ atm at $t = 0$. as a method for evaluating the efficiency of a polymer with respect to duration of zero-order driving force, the percent of water uptake was selected before the water flux values decreased to 90% of their initial values. The value of the initial slope for the equation of a straight line emanating from the percent weight gained axis will be equal to the initial value of dy/dt evaluated at $t = 0$, with the y intercept c defining the linear swelling time, with $(dy/dt)0 = 0.665$ and the y intercept = 0.359, which yields $y = 0.665t + 0.359$. In order to determine when the value of the cumulative water uptake is 90% below the initial rate, the following expression is solved for t:

$$0.9 = (at^2 + bt + c)/(bt + c) = (\Delta wt/wt)0.9(-0.00106t^2 + 0.665t + 0.359)/(0.665t + 0.359) = 0.9,$$

and solving for t $$-0.00106t^2 + 0.0065t + 0.0359 = 0$$

$$t = (-0.0065 \pm](0.0665)^2 - 4(-0.00106) (0.0359)]^{\frac{1}{2}}/2(-0.00106)$$

$t = 62$ min and the weight gain is $-0.00106(62)^2 + (0.665)$ $(62) + 0.359 = 38$ µl with the initial sample weight = 100 mg. thus ($\Delta$ wt/wt). $9 \times 100 = 38\%$ Other methods available for studying the hydrogel solution interface include rheologic analysis, viscometric analysis, elipsometry, contact angle measurements, electokinetic determinations, infared spectroscopy, optical microscopy, interface morphology and microscopic examination of an operative device.

The solubility of beneficial agent formulation, including a medicine, in a fluid that enters the compartment can be determined by known techniques. One method consists of preparing a saturated solution comprising the fluid plus the medicine and ascertained by analyzing the amount of medicine present in a definite quantity of the fluids. A simple apparatus for this purpose consists of a test tube of medium size fastened upright in a water bath maintained at constant temperature and pressure, in which the fluid and medicine are placed and stirred by a rotating glass spiral. After a given period of stirring, a weight of the fluid is analyzed and the stirring continued an additional period of time. If the analysis shows no increase of dissolved medicine after successive periods of stirring, in the presence of excess solid medicine in the fluid, the solution is saturated and the results are taken as the solubility of the product in the fluid. If the medicine is soluble, an added osmotically effective compound optionally may not be needed. If the medicine has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in *United States Public Health Service Bulletin*, No. 67 of the Hygenic Laboratory; *Encyclopedia of Science and Technology*, Vol. 12, pp 542–556, 1971, published by McGraw-Hill, Inc.,; and *Encyclopedia Dictionary of Physics*, Vol. 6, pp 547–557, 1962, published by Pergammon Press, Inc.

The expression osmotic passageway as used herein denotes a laser drilled passageway through wall 12 to form passageway 18. The expression also denotes a passageway laser drilled through wall 12 to form passageway 19 sealed by means 20. Osmotic passageway 18 will pass through wall 12 for communication with compartment 13 for delivering beneficial agent 14. The laser, when drilling passageway 19, drills through wall 12 and an extra 1 to 10 mils (0.125 mm to 0.256 mm) for activating means 17 for forming closure 20. Generally for the purpose of this invention, the passageway will have a maximum cross-sectional area, A, defined by the equation:

$$\frac{L}{F} \times \frac{Qv}{t} \times \frac{1}{DS}$$

wherein L is the length of the passageway, (Qv/t) is the mass delivery rate of the agent D released per unit of time, D is the diffusion coefficient of the medicine in the release solution, S is the solubility of the medicine in the fluid and F has a value of approximately 2 to 1000, said osmotic passageway having a minimum area, $A_s$, defined by equation:

$$\left[\frac{Lv}{t} \times 8 \times \frac{\pi \eta}{\Delta P}\right]^{\frac{1}{2}}$$

wherein L is the length of the passageway, v/t is the volume of the medicine released per unit of time, $\pi$ is 3.14, $\eta$ is the viscosity of the solution being released, and $\Delta P$ is the hydrostatic pressure difference between the inside and the outside of the compartment and having a value up to 20 atm. The dimension for the osmotic passageway is disclosed in U.S. Pat. No. 3,916,899. Laser drilling machines with photo detectors are disclosed in U.S. Pat. No. 4,088,864. Laser equipment is commercially available from Coherent Radiation of California and from Photon Sources of Michigan.

The device of the invention is manufactured by standard techniques. For example, in one embodiment, the agent and other ingredients that may be housed in one area of the compartment adjacent to the passageway are pressed into a solid possessing dimension that corresponds to the internal dimensions of the area of the compartment the gate will occupy, or the agent and the other ingredient and a solvent are mixed into a solid or semisolid form by conventional methods such as ball-milling, calendering, stirring or rollmilling, and then pressed into a preselected shape. Next, a layer of a hydrogel is placed on contact with the layer of agent in a like manner, and the two layers surrounded with a semipermeable wall. The layering of agent formulation and hydrogel can be fabricated by conventional two-layer press techniques. The wall can be applied by molding, spraying or dipping the pressed shapes into a wall forming material. Another and presently preferred technique that can be used for applying the wall is the air suspension procedure, or, optionally, the pan coating procedure. This procedure consists in suspending and tumbling the pressed agent and dry hydrogel in a current of air and a wall forming composition until the wall is applied to the agent-hydrogel composite. The air suspension procedure is described in U.S. Pat. No. 2,779,241; *J. Am. Pharm. Assoc.* Vol. 48, pp 451–459, 1979; and ibid., Vol 49, pp 82–84, 1960. Other standard manufacturing procedures are described in *Modern Plastics Encyclopedia*, Vol. 46, pp 62–70, 1969; and in *Pharmaceutical Sciences*, by Remington, 14th Ed., pp 1626–1678, 1970, published by Mack Publishing Companying, Easton, PA.

Exemplary solvents suitable for manufacturing the wall and the core include inorganic and organic solvents that do not adversely harm the wall and the core forming material and the final device. The solvents broadly include members selected from the group consisting of aqueous solvents, alcohols, ketones, esters, ethers aliphatic hydrocarbons, halogenated solvents, cycloaliphatic aromatics, heterocyclic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethelene glycol monoethyl acetate, methylene dichloride, ethylene dichloride, propylene dichloride, carbon tetrachloride, mitroethane, mitropropane, tetrachloroethane, ethyl ether, isopropyl ether, cyclohexane, cyclo-octane, benzene toluene, naptha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol, and the like.

The following example illustrates means and methods for carrying out the present invention. The example is merely illustrative and it should not be considered as limiting the scope of the invention, as this example and other equivalents thereof will become more apparent to those versed in the dispensing art in the light of the present disclosure, the drawings and the accompanying claims.

EXAMPLE 1

An osmotic device for the controlled delivery of a beneficial medicine formulation is manufactured as follows: First, 40 grams of haloperidol are mixed with 940 grams of poly(ethylene oxide) having a molecular weight of 100,000 to produce a homogeneous blend. The two ingredients are mixed in a V-blender for 1 hour and then transferred to a Hobart ® mixer. Next, 920 millileters of absolute ethanol is slowly added to the mixer and the mixing continued for 15 to 20 minutes at low speed for producing wet granules. The wet granules are dried at 22° C. for 48 hours and passed through a commercial 20 mesh screen. Next, the granules are placed in a V-blender and lubricated with 20 grams of magnesium stearate for 10 minutes.

Next, 598.5 grams of poly(ethylene oxide) coagulant having a molecular weight of 5,000,000 is blended with 275.5 grams of sodium chloride, and 47.5 grams of hydroxypropyl methylcellulose in a V-blender for 1 hour and then transferred to the mixer. Next, 931 millileters of denatured alcohol is slowly added to the mixer and the ingredients slowly mixed for 15 to 20 minutes to yield wet granules. The wet granules are dried at 22° C. for 50 hours, and then passed through a 20 mesh screen. Next, the dry granules are returned to the V-blender and 50 grams of Fischer-Tropich wax, microfine, added to the blender followed by the addition of 19 grams of magnesium stearate. Finely, all the ingredients are blended for 10 to 15 minutes at room temperature.

Next, 275 milligrams of the medicine formulation is added to a Manesty Press and pressed to form a medicine formulation layer. Then, 192.5 milligrams of the hydrogel wax formulation is added to the Manesty Press and pressed to form a layer of hydrogel formulation in contact with the layer of medicinal formulation.

Next, the bilayer compartment forming member is surrounded with a semipermeable wall. The semipermeable wall weighs 32 milligrams and comprises 90 wt:percent of cellulose acetate having an acetyl content of 39.8% and 10 wt:percent polyethylene glycol having a molecular weight of 3350. The semipermeable membrane is applied in an Aeromatic air suspension coater. The coating solution consisted of cellulose acetate having an acetyl content of 39.8% and polyethylene glycol 3350 dissolved in acetone:water (90:10 by wt) to give 4% solid sprayed around the bilayer compartment. The semipermeable coated systems are dried in a forced air oven at 45° C. for 35 hours to evaporate the solvents.

Next, the dried osmotic systems are divided into two groups. The first group of osmotic systems are visually inspected and laser drilled on the medicine formulation side only to give an osmotic passageway of 0.36 millimeters. The second group of osmotic systems are laser drilled on both the medicine formulation side and on the hydrogel means side to give a 0.36 millimeter passageway.

Figure 4A:
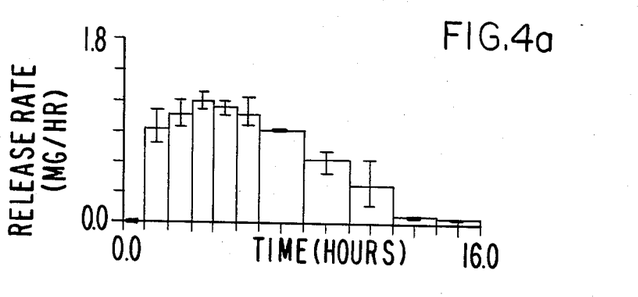
Figure 4B:
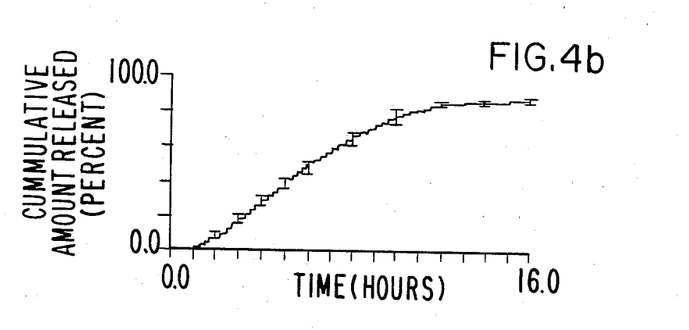
Figure 5A:
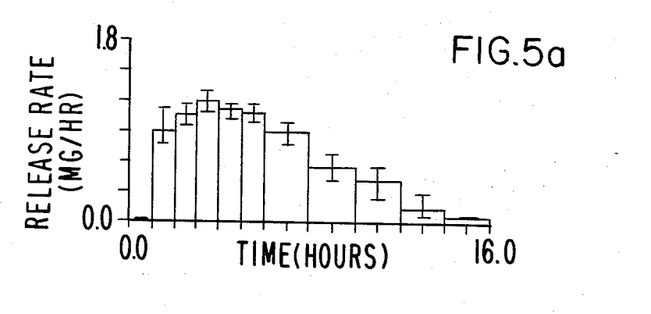
Figure 5B:
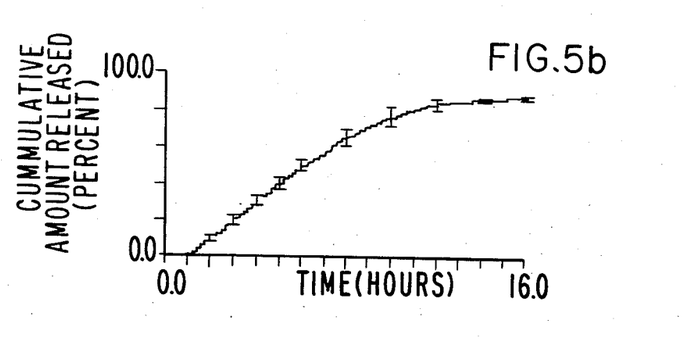

The first group and the second group of osmotic systems are placed in an artificial gastric fluid at 37° C. to ascertain their release rates. The results of the study indicated both groups had similar release rate properties for haloperidol for 14 hours. Also, the 16 hour average cumulative amount of haloperidol delivered was substantially the same for both groups. The measured results for the first group are depicted in FIGS. 4a and 4b, and the measured results for the second group are depicted in FIGS. 5a and 5b. In the Figures, the bars represent the minimum and maximum spread of the measured points.

EXAMPLE 2

The manufacturing procedure as set forth in FIG. 1 is repeated in this example. In this example all the conditions are as previously described, except that the osmotic devices are made without any means for sealing the passageway. The osmotic devices are divided into two groups, one group comprising a single laser drilled passageway communicating with the medicinal formulation layer, and the other group comprising an osmotic passageway communicating with the medicinal formulation and a passageway communicating with the hydrogel layer.

Figure 6A:
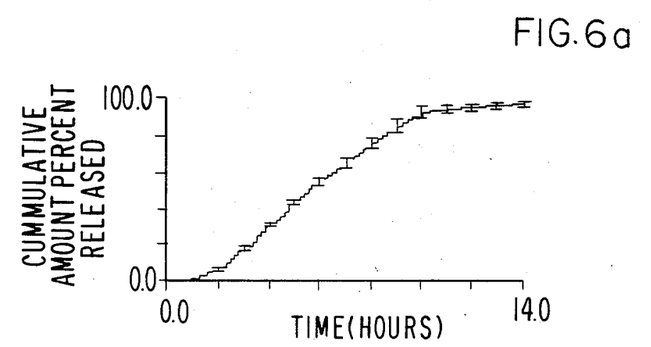
Figure 6B:
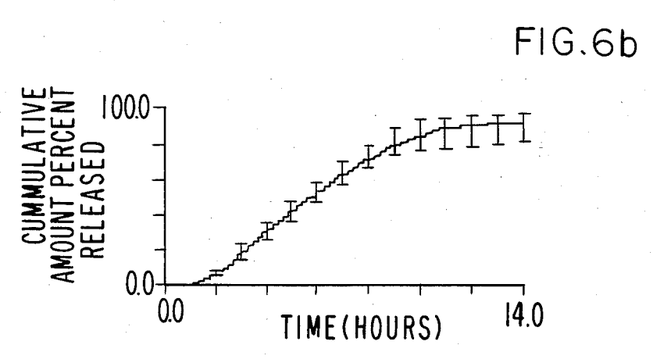

The cumulative amount of medicine, haloperidol, released over time is measured for each group in artificial gastric juice. The artificial gastric juice is prepared according to the procedure in *United States Pharmacopeia*, Vol. XVI, p 1424, 1985, published by the United States Pharmacopecial Convention, Inc., Rockville, MD. The results of the test are set forth in FIGS. 6a and 6b. The results indicate an osmotic device with a single passageway had a cumulative amount of haloperidol release of 10.7 mg over a prolonged period of 14 hours. The results indicated also the osmotic device with the two passageways exhibited a cumulative amount of haloperidol release of 10.1 mg over the same prolonged period of 14 hours. These results indicate the effectiveness of the sealing means for, in the absence of said means, some hydrogel and socium chloride ooze from the device, thereby decreasing the applied force available for urging the medicine formulation from the osmotic device.

EXAMPLE 3

An osmotic therapeutic device for the controlled and continuous oral release of the beneficial drug oxprenolol hydrochloride is made as follows: 250 mg of oxprenolol hydrochloride, 10.7 mg of polyvinyl pyrrolidone, and 8 mg of magnesium stearate are mixed thoroughly and pressed in a Manesty press with a 7/16 inch punch using a pressure head of one and one-half tons to produce a layer of the drug composition. Next, 290 mg of polyacrylamide, commercially available under the name Cyanamer®A-370, a hydrogel polymer of approximately 200,000 mol. wt, is blended with 10 mg of carnauba wax, MP 86°-87° C., and the blend added to the Manesty press and pressed to form a layer of expandable hydrogel in contact with the layer of drug formulation.

Next, a semipermeable wall is formed by blending 170 g of cellulose acetate having an acetyl content of 39.8% with 400 ml of methylene chloride and 400 ml of methanol, and spray coating the two layered compartment forming members in an air suspension machine having a 1.8 kg charge until a 5.1 mil thick semipermeable wall surrounds the compartment. The semipermeable wall coated device is dried for 50 hours at 45° C. Then, a first laser drilled passageway is drilled through the semipermeable wall connecting the drug formulation with the exterior of the device. The device is turned over and a second passageway is drilled through the wall and it immediately seals under the influence of laser energy on the wax. The osmotic device release drug through the single opened passageway over time.

EXAMPLE 4

An osmotic therapeutic device manufactured in the form of an oral delivery device for delivering oxtriphylline to the gastrointestinal tract is manufactured as follows: First, 300 mg of a medicinal composition comprising 95% oxtriphylline, 4% polyvinyl pyrrolidone and 1% magnesium stearate is prepared by blending the ingredients into a homogeneous blend, and then pressing the blend into a solid mass in a Manesty machine.

Next, 55 mg of lightly cross-linked polyethylene oxide and 5 mg of microcrystalline myrtle wax, MP 39°-43° C., are blended together and the blend added to the Manesty machine directly in contact with the previously added drug formulation. Then, pressure is applied and the blend pressed into a solid mass. Then, the two-layered mass is coated in a standard air suspension machine with a semipermeable polymeric wall formed from a 5% solution consisting of cellulose acetate having an acetyl content of 38.3% in a solvent consisting of acetone and water, 95:5 wt:wt. The semipermeable wall of the osmotic device is 7.3 mils thick. Finally, an osmotic passageway having a diameter of 10 mils is laser drilled through the semipermeable wall facing the oxtriphylline formulation for delivering it from the device. Then, the device is inverted, and a passageway drilled through the opposite surface upon the application of laser energy.

EXAMPLE 5

An osmotic therapeutic device manufactured in the form of an oral osmotic device for delivering indomethacin is manufactured by following the procedures of Examples 3 and 4. The layer of drug formulation weighs 225 mg and it comprises 45% sodium indomethacin, 57% sucrose, 1% magnesium stearate and 7% agar. The hydrogel layer weighs 120 mg and it comprises 95% lightly cross-linked poly(ethylene oxide), mol. wt 500,000. The bilayers are surrounded with a semipermeable wall 5 mils thick. The wall comprises 91% cellulose acetate having an acetyl content of 32% and 8% sorbitol, formed from a solvent consisting essentially of 360 ml of water and 3,470 ml of acetone. The open osmotic passageway has a diameter of 8.1 mils. The opposite surface of the device has a closed passageway formed during the manufacture of the osmotic device.

The novel osmotic systems of this invention use means for the obtainment of precise release rates in the environment of use while simultaneously maintaining the integrity and character of the system. While there has been described and pointed out features of the invention as applied to presently preferred embodiments, those skilled in the art will appreciate that various modifications, changes, additions and omissions in the system illustrated and described can be made without departing from the spirit of the invention.

I claim:

1. An osmotic dispensing device for delivering a beneficial medicine formulation to an environment of use, comprising:
   (a) a wall comprising at least in part a semipermeable composition permeable to the passage of an exterior fluid present in the environment of use and substantially impermeable to the passage of the beneficial medicine formulation, which wall surrounds and forms:
   (b) a compartment;
   (c) a first passageway in the wall;
   (d) a second passageway in the wall;
   (e) a first layer comprising a beneficial medicine formulation in the compartment communicating with the first passageway;
   (f) a second layer comprising an expandable osmopolymer in the compartment, said second layer in communication with the second passageway; and
   (g) means possessing the ability to flow, form a film and seal the second passageway in the second layer for closing the second passageway during manufacture of the osmotic device.

2. A process for manufacturing an osmotic dispensing device for delivering a medicine to a fluid environment of use, the process comprising:
   (a) compressing a beneficial medicine formulation into a layer;
   (b) compressing a composition comprising a hydrogel and a means for closing a passageway formed during the manufacture of the osmotic device in a layer in contact with the layer comprising the beneficial medicine formulation;
   (c) surrounding the compressed contacting layer with a semipermeable wall;
   (d) laser drilling a passageway in the wall connecting the exterior of the device with the layer of beneficial medicine formulation for releasing the medicine formulation through the passageway from the device;
   (e) laser drilling a passageway in the wall distant from the passageway connected to the medicine formulation; and,
   (f) closing the passageway in the wall distant from the passageway connected to the medicine formulation by applying laser energy to the means for closing the passageway, whereby the means closes said passageway.

* * * * *